United States Patent [19]

Labovitz et al.

[11] Patent Number: 4,729,782
[45] Date of Patent: * Mar. 8, 1988

[54] POLLEN SUPPRESSANT COMPRISING A FUSED PYRIDAZINONE

[75] Inventors: Jeffrey N. Labovitz, Palo Alto; Lawrence Fang, Foster City, both of Calif.

[73] Assignee: Lafarge Coppee, Paris, France

[*] Notice: The portion of the term of this patent subsequent to Aug. 5, 2003 has been disclaimed.

[21] Appl. No.: 717,666

[22] Filed: Mar. 29, 1985

Related U.S. Application Data

[63] Continuation-in-part of Ser. No. 532,020, Sep. 14, 1983, Pat. No. 4,604,134.

[51] Int. Cl.$^4$ .................... A01N 43/58; C07D 237/28
[52] U.S. Cl. ................................................ 71/92; 544/235
[58] Field of Search ................................ 71/92; 544/235

[56] References Cited

U.S. PATENT DOCUMENTS

| 4,009,020 | 2/1972 | Starke et al. | 71/94 |
| 4,115,101 | 9/1978 | Carlson | 71/94 |
| 4,345,934 | 8/1982 | Fujimoto | 71/92 |

FOREIGN PATENT DOCUMENTS

| 0220776 | 6/1956 | Australia | 71/92 |
| 0037133 | 10/1981 | European Pat. Off. | 71/92 |
| 2400832 | 3/1979 | France | 71/92 |

OTHER PUBLICATIONS

Ames et al., "Synthesis of 1-Aryl-4-Oxo-1H,4H-Cinnoline-3-Carboxylic Acid Esters," Chem. Abs. 98: 143356 (1983).
Prudchenko et al., "Reactions of Ethyl Pentafluorobenzoylacetate", Chem. Abs. 69: 36059q (1968).
Kamebo Ltd., "6-Fluoro-1,4-Dihydro-4-Oxocinnoline-3-Carboxylic Acid Derivatives", Chem. Abs. 98: 126137s (1983).

Primary Examiner—Glennon H. Hollrah
Assistant Examiner—Patricia L. Morris
Attorney, Agent, or Firm—Leydig, Voit & Mayer

[57] ABSTRACT

Pollen suppressants of the formula

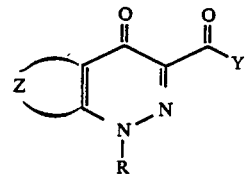

wherein Z represents a divalent organic radical of the formula —CH=CH—CH=CH—, —CH=CH—CH=N—, —CH=CH—N=CH—, —CH=CH—NH—, —CH=CH—O, or —CH=CH—S— or said radical in which an H of Z is replaced with a halogen atom with the proviso that no more than three H of Z are replaced by fluorine; a $C_1$-$C_4$ alkyl, $C_1$-$C_4$ alkoxy, $C_1$-$C_4$ alkanoyl, cyano, nitro, hydroxy, or trihalomethyl group; or a group of the formula —$NR^1R^2$ wherein $R^1$ and $R^2$ independently represent a hydrogen atom or a $C_1$-$C_4$ alkyl group; Y is $Y^1R^3$ or $NR^4R^5$ wherein $Y^1$ is oxygen or sulfur; $R^3$ is hydrogen, $C_1$-$C_4$ alkyl, $C_2$-$C_4$ alkenyl, $C_2$-$C_4$ alkynyl, $C_1$-$C_4$ alkoxyalkyl, cyclohexylmethyl, halogenated $C_1$-$C_4$ alkyl, phenyl, or benzyl; and $R^4$ and $R^5$ are independently selected from the group consisting of hydrogen, $C_1$-$C_4$ alkyl, $C_2$-$C_4$ alkenyl, $C_2$-$C_4$ alkynyl, or $C_1$-$C_4$ alkyl substituted with carboxyl or $C_1$-$C_4$ alkoxycarbonyl; and R represents $C_1$-$C_4$ alkyl, phenyl, naphthyl, or phenyl or naphthyl substituted with one to three substituents selected from the group consisting of halogen, trihalomethyl, $C_1$-$C_4$ alkoxy, $C_1$-$C_4$ alkyl, and cyano, are disclosed along with methods of producing these compounds and of using them to produce hybrid seed in self-fertilizing plants.

41 Claims, No Drawings

POLLEN SUPPRESSANT COMPRISING A FUSED PYRIDAZINONE

This is a continuation-in-part of application Ser. No. 532,020, filed Sept. 14, 1983, now U.S. Pat. No. 4,604,134.

BACKGROUND OF THE INVENTION

1. Field of the Invention

The present invention relates to fused pyridazinone compounds, a process for their preparation, compositions containing these compounds, and a method of regulating the growth of plants using such compounds.

2. Description of the Prior Art

Although genetic manipulation of plants through cross-breeding is a well-known process, hybrids of self-pollinating plants had been difficult to produce. In some cases, e.g., corn, intensive hand labor is required to prevent self-pollinating but is possible because the male and female flower parts are distant from each other on the corn stalk. However, in other plants, e.g., wheat, the male and female plant parts are contained within the same flower and self-pollination is difficult if not impossible to prevent. In wheat, the male stamen produces pollen inside a closed flower. The pollen then falls within the closed flower onto the female stigma. Only after this self-pollination step does the flower open to release extra pollen. Mechanical prevention of self-pollination as is practiced in corn is accordingly impossible in a plant such as wheat.

Nevertheless, it is possible to inhibit self-pollination in wheat and similar plants by chemically inhibiting the formation of pollen or by inducing the plant to produce non-functioning pollen. Several compounds have previously been developed which produce these effects.

DOS 28 08 795 discloses compounds of the formula:

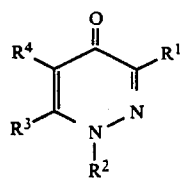

in which $R^1$ is carboxy, a carboxy salt, or an alkoxy carbonyl group, $R^2$ is a substituted phenyl group, $R^3$ is alkyl, and $R^4$ is hydrogen, alkyl or halogen. These compounds are disclosed to be pollen suppressants.

Published European Patent Application No. 0 037 133 discloses compounds of the formula:

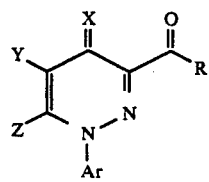

in which X represents oxygen or sulfur, Y represents hydrogen, halogen or an alkyl group, Z represents an alkyl group, Ar represents an optionally substituted phenyl group, and R represents a group which may be, among others $NR^1R^2$ or $ONR^1R^2$ in which $R^1$ can be hydrogen and $R^2$ can be an alkoxy group, an acyl group derived from a carboxylic or carbamic acid, or an alkyl group substituted with a carboxylic acid or ester group. These compounds are also disclosed to be pollen suppressants.

Published European Patent Application No. 0 049 971 discloses compounds of the formula:

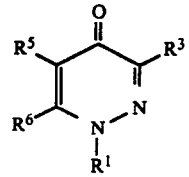

in which $R^1$ can be phenyl substituted with a halogen, $R^3$ can be carboxy or an alkali metal salt thereof, an alkoxy carbonyl, or a substituted carbamoyl, $R^5$ is a carboxy derivative of the type defined for $R^3$, and $R^6$ is a $C_1$-$C_4$ alkyl group. These compounds are disclosed to be chemical hybridizing agents which operate by causing male sterility.

U.S. Pat. No. 4,345,934 discloses a compound of the formula

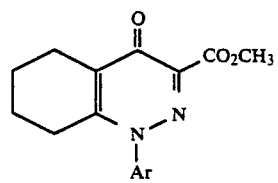

where Ar is 4-chlorophenyl and an attempt to use this compound as a pollen suppressant. However, this compound was not active as a gametocide.

Zh. Obshch. Khim., 37, 2487 (1967), as abstracted in Chem. Abstracts, 69, 36059 (1968), discloses a compound of the formula:

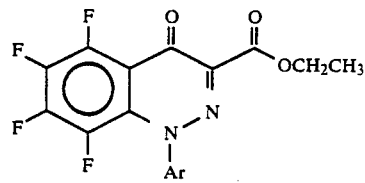

where Ar is phenyl substituted with halogen. However, this publication is directed only to synthesis and no use for the compound is disclosed.

Nevertheless, many of the compounds so tested have adverse effects on hybrid seed quality or injure plants at doses only slightly above those required to produce maximum male plant sterility. Accordingly, a continued need for new pollen suppressants useful for producing hybrid seed of cereal grain exists.

SUMMARY OF THE INVENTION

Accordingly, it is an object of this invention to provide chemical sterilants for producing hybrid seed of cereal grain plants.

It is a further object of this invention to provide a method of suppressing pollen production in cereal grain plants using these compounds.

It is still a further object of this invention to provide a method for producing hybrid seed of cereal grain plants using the novel chemical sterilants of the invention.

These and other objects of the invention as will hereinafter become more readily apparent have been accomplished by providing a chemical pollen suppressant of the formula:

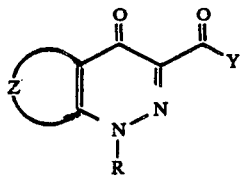

wherein

Z represents a divalent organic radical of the formula —CH=CH—CH=CH—, —CH=CH—CH=N—, —CH=CH—N=CH—, —CH=CH—NH—, —CH=CH—O—, or —CH=CH—S— or said radical in which an H of Z is replaced with a halogen atom with the proviso that no more than three H of Z are replaced by fluorine; a $C_1$–$C_4$ alkyl, $C_1C_4$ alkoxy, $C_1$–$C_4$ alkanoyl, cyano, nitro, hydroxy, or trihalomethyl group; or a group of the formula —$NR^1R^2$ wherein $R^1$ and $R^2$ independently represent a hydrogen atom or a $C_1$–$C_4$ alkyl group;

Y is $Y^1R^3$ or $NR^4R^5$ wherein $Y^1$ is oxygen or sulfur; $R^3$ is hydrogen, $C_1$–$C_4$ alkyl, $C_1$–$C_4$ alkoxyalkyl, cyclohexylmethyl, halogenated $C_1$–$C_4$ alkyl, phenyl, or benzyl; and $R^4$ and $R^5$ are independently selected from the group consisting of hydrogen, $C_1$–$C_4$ alkyl, or $C_1$–$C_4$ alkyl substituted with carboxyl or $C_1$–$C_4$ alkoxycarbonyl; and R represents $C_1$–$C_4$ alkyl, phenyl, naphthyl, or phenyl or naphthyl substituted with one to three substituents selected from the group consisting of halogen, trihalomethyl, $C_1$–$C_4$ alkoxy, $C_1$–$C_4$ alkyl, and cyano.

DESCRIPTION OF THE PREFERRED EMBODIMENTS

The present invention provides novel fused pyridazines in which a non-basic aromatic ring is fused through C-5 and C-6 of the pyridazinone ring. Thus, the chemical pollen suppressants of the invention include those compounds having the formula:

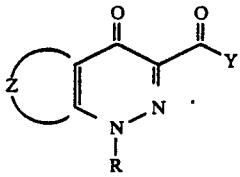

wherein

Z represents a divalent organic radical of the formula —CH=CH—CH=CH—, —CH=CH—CH=N—, —CH=CH—N=CH—, —CH=CH—NH—, —CH=CH—O—, or —CH=CH—S— or said radical in which an H of Z is replaced with a halogen atom with the proviso that no more than three H of Z are replaced by fluorine; a $C_1$–$C_4$ alkyl, $C_1$–$C_4$ alkoxy, $C_1$–$C_4$ alkanoyl, cyano, nitro, hydroxy, or trihalomethyl group; or a group of the formula —$NR^1R^2$ wherein $R^1$ and $R^2$ independently represent a hydrogen atom or a $C_1$–$C_4$ alkyl group;

Y is $Y^1R^3$ or $NR^4R^5$ wherein $Y^1$ is oxygen or sulfur; $R^3$ is hydrogen, $C_1$–$C_4$ alkyl, $C_1$–$C_4$ alkenyl, $C_1$–$C_4$ alkynyl, $C_1$–$C_4$ alkoxyalkyl, cyclohexylmethyl, halogenated $C_1$–$C_4$ alkyl, phenyl, or benzyl; and $R^4$ and $R^5$ are independently selected from the group consisting of hydrogen, $C_1$–$C_4$ alkyl, $C_2$–$C_4$ alkenyl, $C_2$–$C_4$ alkynyl or $C_1$–$C_4$ alkyl substituted with carboxyl or $C_1$–$C_4$ alkoxycarbonyl; and R represents $C_1$–$C_4$ alkyl, phenyl, naphthyl, or phenyl or naphthyl substituted with one to three substituents selected from the group consisting of halogen, trihalomethyl, $C_1$–$C_4$ alkoxy, $C_1$–$C_4$ alkyl, $C_1$–$C_4$ alkanoyl, and cyano.

In one preferred embodiment of the invention, —COY is a carboxy group or a salt thereof. When —COY is a salt of a carboxy group, the cation can be an alkali metal ion, alkaline earth metal ion, or transition metal ion. The cation can also be an ammonium or substituted ammonium ion. Representative alkali metal ions, which are preferred, include lithium, sodium and potassium ions; representative alkaline earth metal ions include magnesium, calcium, and barium ions; representative transition metal ions include zinc, manganese, iron, titanium, and molybdenum ions; and representative ammonium ions include the ammonium ion itself and alkyl-substituted ammonium ions.

Preferred substituents are those in which R represents phenyl or phenyl substituted with one to three substituents selected from the group consisting of halogen, trihalomethyl, $C_1$–$C_4$ alkoxy, $C_1$–$C_4$ alkyl and cyano; more preferably by phenyl substituted with one of said substituents; even more preferably by phenyl substituted with one halogen atom; and most preferably by phenyl substituted with chlorine in the para position; Y is OH, ONa, or OK; and Z represents a divalent organic radical of the formula —CH=CH—CH=CH—, or said radical in which an H of Z is replaced with a halogen atom with the proviso that no more than three H of Z are replaced by fluorine; a $C_1$–$C_4$ alkyl, $C_1$–$C_4$ alkoxy, $C_1$–$C_4$ alkanoyl, cyano, nitro, hydroxy, or trihalomethyl group; or a group of the formula —$NR^1R^2$ wherein $R^1$ and $R^2$ independently represent a hydrogen atom or a $C_1$–$C_4$ alkyl group. Particularly preferred for Z are radicals having one or more hydrogens replaced with halogen and especially those having a halogen, particularly fluorine, at the 5-position of the resulting cinnoline. Such compounds are very active and can be applied during early stages of growth at very low application rates compared to comparable prior art compounds.

Another grouping of preferred substituents includes those in which R represents phenyl or phenyl with substituents selected from the group consisting of 3',4'-dichloro, 3'-trifluoromethyl-4'- chloro, 4'methyl, 4'-methoxy, 4'-trifluoromethyl, 4'-iodo, 4'-chloro, 4'-fluoro, 4'-bromo, 4'-acetyl, 3'-fluoro, 3'-chloro, 3'-trifluoromethyl, and 2'-fluoro. Of these, electro-negative substituents (halogens, trifluoromethyl, and acetyl) are more preferred, especially halogens and trifluoromethyl. With these R substituents, preferred —COY groups are acids and acid salts, although methyl and ethyl esters, amides, and substituted amides are nearly as preferred. Preferred substituted amides include methyl-, ethyl-, propargyl-, diethyl-, and methoxycarbonylmethyl-amides. With these R and Y substituents, Z is preferably a fused benzene ring with an electronegative substituent, preferably halogen or trifluoromethyl and especially fluorine at position 5 of the cinnoline ring.

Preferred compounds are defined by selecting one or more of these listings of preferred substituents in combination with the general formula previously given. Certain combinations of substituents are especially preferred. One preferred grouping occurs when R is phenyl mono-substituted with a halogen; Y is —OH, —ONa, or OK; and Z represents a divalent organic radical of the formula —CH=CH—CH=CH—, or said radical in which an H of Z is replaced with a halogen atom with the proviso that no more than three H of Z are replaced by fluorine; a $C_1$–$C_4$ alkyl, $C_1$–$C_4$ alkoxy, $C_1$–$C_4$ alkanoyl, cyano, nitro, hydroxy, or trihalomethyl group; or a group of the formula —$NR^1R^2$ wherein $R^1$ and $R^2$ independently represent a hydrogen atom or a $C_1$–$C_4$ alkyl group.

Also included within the scope of the invention are agronomically acceptable acid addition salts of compounds having the general formula given. Typical acid addition salts are those formed with strong acids such as hydrochloric, hydrobromic, sulfuric, and nitric acids. Salts of acidic or basic functional-group substituents on Z are also included in this invention. Throughout this application, agronomically acceptable salt means that the salt is not substantially more toxic to the plant or to the consumer of the plant than the parent compound from which the salt is formed.

Typical compounds of the invention include the following:

1-phenyl-1,4-dihydro-4-oxo-5,6,7,8-tetrachlorocinnoline-3-carboxylic acid 1-phenyl-1,4-dihydro-4-oxo-5-trifluoromethylcinnoline-3-carboxylic acid 1-phenyl-1,4-dihydro-4-oxo-7-t-butylcinnoline-3-carboxylic acid 1-(4-chlorophenyl)-1,4-dihydro-4-oxo-5-fluorocinnoline-3-carboxylic acid 1-(4-bromophenyl)-1,4-dihydro-4-oxo-6-nitrocinnoline-3-carboxylic acid 1-(3,4-dichlorophenyl)-1,4-dihydro-4-oxo-8-cyanocinnoline-3-carboxylic acid 1-(4-iodophenyl)-1,4-dihydro-4-oxo-8-acetylcinnoline-3-carboxylic acid 1-(4-fluorophenyl)-1,4-dihydro-4-oxo-6,8-dihydroxycinnoline-3-carboxylic acid 1-(4-chlorophenyl)-1,4-dihydro-4-oxocinnoline-3-carboxylic acid 1-(3-chlorophenyl)-1,4-dihydro-4-oxo-6-dimethylaminocinnoline-3-carboxylic acid 1-(2,4,6-trichlorophenyl)-1,4-dihydro-4-oxothieno[3,2-e]pyridazine-3-carboxylic acid 1-(4-methylphenyl)-1,4-dihydro-4-oxothieno[2,3-e]pyridazine-3-carboxylic acid 1-(4-trifluoromethylphenyl)-1,4-dihydro-4-oxo-6-methylaminopyrido[2,3-e]pyridazine-3-carboxylic acid 1-(3-ethoxyphenyl)-1,4-dihydro-4-oxo-6-ethylthieno[2,3-e]pyridazine-3-carboxylic acid 1-(3-cyanophenyl)-1,4-dihydro-4-oxofuro[2,3-e]pyridazine 1-(2-chloro-4-methylphenyl)-1,4-dihydro-4-oxo-6-chloroimidazo[2,3-e]pyridazine-3-carboxylic acid 1-(2-trifluoromethyl-4-chlorophenyl)-1,4-dihydro-4-oxo-6-methylfuro[3,2-e]pyridazine-3-carboxylic acid 1-(2-trifluoromethyl-4-bromophenyl)-1,4-dihydro-4-oxo-5-trifluoromethylfuro[3,2-e]pyridazine-3-carboxylic acid 1-(2-chloro-5-trifluoromethylphenyl)-1,4-dihydro-4-oxo-7-diethylfuro[3,2-e]pyridazine-3-carboxylic acid 1-(2-naphthyl)-1,4-dihydro-4-oxofuro[3,2-e]pyridazine-3-carboxylic acid as well as the sodium, potassium, and lithium carboxylate salts of each of the above compounds and the acid addition salts of each of the above listed compounds. By carboxylate salt is meant a salt of a carboxylic acid group at C-3. By acid addition salt is meant a salt formed by the protonation of a ring or side chain nitrogen.

The compounds of the invention can be synthesized according to known methods for the production of analogous compounds or can be produced by synthetic modification of known pyridazinones or cinnolines. For example, numerous synthetic pathways to cinnolines and to pyridazines condensed with other heterocyclic rings are disclosed in *Condensed Pyridazines Including Cinnolines and Phthalazines*, R. N. Castle, ed., John Wiley and Sons, N.Y., 1973, pages 1–321 (cinnolines) and 761–1056 (pyridazines condensed with heterocyclic rings) of which are herein incorporated by reference. For example, one suitable method involves the reaction of readily accessible diethyl mesoxalate diphenylhydrazones of the formula:

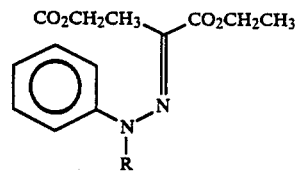

in which R represents one of the groups previously named, with a ethanolic base to give a dicarboxylic acid. This acid is converted into a diacid chloride using a suitable reagent, such as thionyl chloride. The acid chloride then undergoes a Friedel-Crafts acylation reaction, for example in nitrobenzene at about 100° C. in the presence of $TiCl_4$. A product having the following formula is obtained:

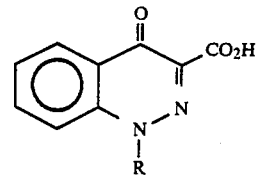

wherein R has the previously given meanings. Although this reaction is shown with an unsubstituted phenyl group for the sake of simplicity, other aromatic rings or substituents may also be present, although at least one ortho position of the diphenylhydrazone must be free in order that the Friedel-Crafts reaction can take place. Groups that would interfere with this ring-forming reaction may be present in protected form (e.g., an acylamino group that may later be converted into an amine) or they may be added later (e.g., by halogenation of the phenyl rings) or they may be prepared by conversion of a suitable group present during synthesis (e.g., the above-mentioned amino group may be diazotized and converted into many different functional groups).

Another general synthetic method for synthesizing compounds of the invention is described in *Synthesis*, pages 52–53 (1983), which is also herein incorporated by reference. In this reaction sequence, the key step is condensation of an intermediate of the formula:

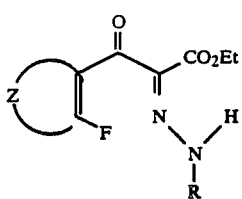

where R has the meanings previously defined and F may optionally be a nitro group rather than fluorine. This reaction is particularly useful for the preparation of cinnolines.

The above-indicated 3-carboxycinnolines (and 3carboxy(e-fused heterocycle)pyridazines which can be synthesized by the same method) can then be converted into other compounds of the invention by known methods. For example, the carboxylic acid group can be converted into a carboxylate salt or a protected amino group can be deprotected, diazotized, and converted into a different functional group.

Various modifications of these reactions and of other reactions capable of modifying the initially formed cyclic compounds can be used to produce all the compounds of the present invention, for example as is disclosed in the four prior art patents previously cited (U.S. Pat. No. 4,345,934, DOS No. 28 08 795, EP No. 37 133, and EP No. 49 971), which are herein incorporated by reference.

A series of compounds has been synthesized using the methods described above, and some of these compounds have been tested for ability to induce male sterility using the procedure set forth in Example 2, which follows. Representative compounds are shown in Table 1 below.

TABLE 1

Synthesized Compounds of the Invention

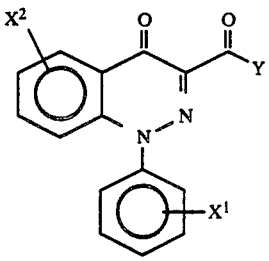

| $X^1$ | $X^2$ | Y | Percent Sterility | Dose (ppm, Stage of Application) | m.p. (°C.) |
|---|---|---|---|---|---|
| 3',4'-diCl | 5-F | —OH | 85 | 25/2 | 188–190° |
| 4'-CH$_3$ | 5-F | —OCH$_2$CH$_3$ | 25 | 40/1 | 124–127° |
| 4'-CH$_3$ | 5-F | —OH | 30 | 60/1 | — |
| 4'-OCH$_3$ | 5-F | —OH | 32 | 60/1 | — |
| 4'-OCH$_3$ | 5-F | —OCH$_2$CH$_3$ | 30 | 60/1 | 151–154° |
| 4'-CF$_3$ | 5-F | —OCH$_2$CH$_3$ | 100 | 60/3 | 196–198° |
| 4'-I | 5-F | —OH | 100 | 80/1 | — |
| 4'-I | 5-F | —OCH$_2$CH$_3$ | 98 | 80/1 | 179–181° |
| 4'-Cl | 5-Cl | —OH | 80 | 80/1 | — |
| 4'-Cl | 5-Cl | —OCH$_2$CH$_3$ | 40 | 40/1 | 148–150° |
| 4'-F | 5-F | —OH | 100 | 25/1 | 219° (dec.) |
| 4'-F | 5-F | —OCH$_2$CH$_3$ | — | — | 168–170° |
| 3'-F | 5-F | —OH | 98 | 100/2 | — |
| 3'-F | 5-F | —OCH$_2$CH$_3$ | 85 | 100/2 | 185–187° |
| 3'-Cl | 5-F | —OH | 50 | 100/2 | — |
| 3'-Cl | 5-F | —OCH$_2$CH$_3$ | — | — | 189–190° |
| H | 5-F | —OCH$_2$CH$_3$ | 90 | 25/2 | — |
| H | 5-Cl | —OH | 100 | 50/2 | — |
| H | 5-Cl | —OCH$_2$CH$_3$ | — | — | 128–130° |
| 2'-F | 5-F | —OH | 100 | 50/3 | 220–222° |
| 2'-F | 5-F | —OCH$_3$ | — | — | — |
| 3'-CF$_3$ | 5-F | —OH | 92 | 250/2 | 259–261° |
| 3'-CF$_3$ | 5-F | —OCH$_3$ | — | — | 196–198° |
| 4'-Br | 5-F | —OH | — | — | 251–253° |
| 4'-Br | 5-F | —OCH$_2$CH$_3$ | — | — | 195–197° |
| 4'-Cl | 5-F | —NCH$_2$CH=CH$_2$ (H) | — | — | 228–230° |
| 4'-Cl | 5-F | —NH$_2$ | — | — | 224–227° |
| 4'-CCH$_3$ (O) | 5-F | —OCH$_3$ | — | — | 185–185° |
| 4'-Cl | 5-F | —NHCH$_3$ | — | — | 217–219° |
| 4'-Cl | 5-F | —NHCH$_2$CH$_3$ | — | — | 195–197° |
| 3'-CF$_3$, 4'-Cl | 5-F | —OCH$_3$ | — | — | 185–188° |
| 4'-Cl | 5-F | —N(CH$_2$CH$_3$)$_2$ | — | — | 223–225° |
| 4'-CF$_3$ | 5-F | —N(CH$_2$CH$_3$)$_2$ | — | — | 228–230° |
| 4'-CF$_3$ | 5-F | —NHCH$_2$CH$_3$ | — | — | 227–229° |

TABLE 1-continued
Synthesized Compounds of the Invention

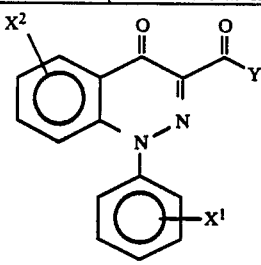

| $X^1$ | $X^2$ | Y | Percent Sterility | Dose (ppm) Stage of Application | m.p. (°C.) |
|---|---|---|---|---|---|
| 4'-Cl | 5-F | —NHCH$_2$COOCH$_3$ | — | — | — |

Compounds of the invention are useful as chemical hybridization agents in graminaceous crops, such as wheat, barley, maze, rice, sorghum, millet, oats, rye, triticale, forage crops and the like. Of these, treatment of wheat is preferred. Different plant growth regulating effects will be obtained depending upon the growth stage of the plant when treated. Compounds of the invention induce selected male sterility without also inducing unacceptable female sterility. About 30% female fertility is generally acceptable, although this level may differ when the method is used commercially, based on the economics of $F_1$ seed production. As used herein, the term male sterility includes sterility caused by lack of male flower parts, by formation of sterile pollen, and by male flower parts which produce normal pollen but are functionally unable to cause pollination. Where the male sterility of compounds of the invention is accompanied by female infertility of an unacceptable level or by phytotoxicity, compounds are still minimally useful in production of ergot, for example as described in French Published Patent Application No. 2400832, which is herein incorporated by reference. When compounds of the invention are used in hybridization, they are used in an amount sufficient to produce the effect of male sterility without producing a phytotoxic reaction or other undesired side-reaction. Compounds of the invention are generally applied at a rate of from 0.025 to 20.0 pounds per acre, and preferably from 0.125 to 10.0 pounds per acre. The amount used depends upon the plant type and the method of application as is well-known to those skilled in the art and can be determined by simple experimentation if not known.

Although any method of hybridization may be used, the following method generally is sufficient. The two parent strains to be crossed are planted in alternate sections, rows, or groups of rows. The female parent is treated with a compound of the invention in order to render this parent male sterile. Pollen from the male (untreated) parent then fertilizes the female parent, either by means of human intervention or preferably by means of a natural process, such as wind-borne pollination. The seed produced by the female parent is an F-1 hybrid, which is then collected according to conventional techniques.

One method of applying the compounds of the invention in the previously-mentioned hybridization technique or for otherwise inducing male sterility is application directly to the plant leaves. When this method is used, very selective male sterility can be obtained when the compound is applied between the beginning of bloom and the beginning of meiosis. Compounds of the invention can also be applied directly to seed in order to cause male sterility, whereby the seeds are dipped into a fluid formulation containing the active ingredient. Seed can also be sprayed with a solution or suspension containing a compound of the invention. In general, seed are treated with a compound of the invention in an amount of from about ¼ to 10 pounds per 100 pounds of seed. Compounds of the invention are also effective when they are applied to the medium in which plants are grown such as soil or the water surface in a rice field.

Compounds of the invention can be used as hybridization materials together with other plant regulatory agents, for example, in mixtures with these compounds. Examples of plant regulating materials which can be used include auxins, gibberellins, ethylene liberating materials such as Ethephon, pyridones, cytokinins, maleic hydrazide, carbonic acid, 2,2dimethyl hydrazide, cholines (as well as their salts), (2-chloroethyl)trimethylammonium chloride, triiodobenzoic acid, tributyl-2,4-dichlorobenzenephosphonium chloride, polymeric N-vinyl-2oxazolidinones, tri(dimethylaminoethyl)phosphate, and salts of these compounds as well as N-dimethylamino 1,2,3,6-tetrahydrophthalamides and their salts. Compositions containing one or more compounds of the invention in a 1:99–99:1 ratio to one or more different compounds having plant regulatory activities may be prepared. Likewise, compounds of the invention may be prepared into compositions useful for other agricultural purposes, such as herbicides, fungicides, insecticides, and plant bactericides.

A compound of the invention can be applied to a plant either as itself or in combination with other plant growth regulators. A composition containing a compound of the invention and any other active ingredient may be diluted with an agronomically suitable carrier, which is any substance which itself is without any significant effect on plants but which is added in order to allow simpler application of the active ingredients to plants. Carriers include both liquids and solids. Accordingly, compositions of the invention can be either solid or liquid formulations or solutions. For example, the compounds can be used in powders, emulsifiable concentrates, dusts, pellets, aerosols and solutions. In any of the various formulations, a surface active agent may be added in order to increase uptake of the active compounds. It is especially preferred, and particular for methods which involve application to leaves, to utilize agents which aid in the application of the material, for example, dispersion agents and detergents.

Compounds of the invention can be dissolved in any suitable solvent. Examples of solvents which can be used include water, alcohols, ketones, aromatic hydrocarbons, halogenated hydrocarbons, dimethylformamide, dioxane, and dimethylsulfoxide. Mixtures of these solvents can likewise be used. The concentration of these solutions can be from about 2 to about 98% by weight of active ingredient and is preferred to be in the range from about 20 to about 75% by weight.

In order to produce emulsifiable concentrates, the compounds of the invention are dissolved in an organic solvent, such as benzene, toluene, xylene, methylated naphthalene, corn oil, terpentine, o-dichlorobenzene, isophorone, cyclohexane, or methyl oleate or in mixtures of these solvents, together with an emulsifying material which allows the dispersion in water. Suitable emulsifying agents include ethylene oxide derivatives of alkylphenols or long-chained alcohols, mercaptans, carboxylic acids, and reactive amines, and especially high molecular weight alcohols. Solvent-soluble sulfates or sulfonates, such as the alkaline earth salts or amine salts of alkylbenzenesulfonates as well as sodium fatty alcohol sulfates with surface active properties can be utilized as emulsifying agents either alone or in combination with an ethylene oxide reaction product. Free-flowing emulsion concentrates are formulated similarly to emulsifiable concentrates and contain, in addition to the previously described components, water as well as a stabilizing agent, such as a water-soluble cellulose derivative or a water-soluble salt of a polyacrylic acid. The concentration of the active ingredient in the emulsifiable concentrate is generally about 10 to 60 wt. % and in free-flowing emulsion concentrates is generally about 10 to 60% or sometimes up to 75% by weight.

When a powder containing the compound of the invention is being prepared, the active ingredient is usually mixed with a finely divided solid, such as a clay, an organic silicate or carbonate, or a silica gel along with an agent capable of holding together the resulting materials. The concentration of the active ingredient in such powders generally lies between about 20 and 98% by weight and preferably lies between 40 and 75% by weight. A dispersion material can generally be present in an amount of about 0.5 to 3% by weight of the entire powder. An agent may be added in order to control water absorption and if added is generally present in an amount of about 0.1 to about 5% by weight of the total powder.

Dusts can be prepared by mixing the active ingredient with a finely divided inert solid, which can be of an organic or inorganic nature. Suitable material for this purpose include flour, farina, diatomite, silicates, carbonates, and clays. A satisfactory method for the production of dusts involves crushing a wettable powder together with a finely divided carrier. A dust concentrate, which contains from about 20 to about 80% of the active ingredient, is produced according to known methods and then diluted to form a final concentration of the compound of the invention of about 1 to about 10% by weight of the dust.

Particulate formulations can be prepared by any known method, for example by impregnating the active ingredient into a solid material, such as particulate Fullers earth, vermiculite, cornmeal, seed hulls such as grain hulls, or other materials. A solution of one or more of the compounds of the invention in a freely flowing organic solvent can be applied to the particulate solid or mixed therewith, after which the solvent is evaporated away. The particulate material is not limited to a particular size. However, a useful size is from 16 to 60 mesh (U.S. standard mesh size). The active ingredient generally occupies about 2 to about 15 wt % of the particulate formulation.

Salts of the compounds of the invention can be prepared as aqueous solutions and applied in this form. The salts occupy typically about 0.05 to about 50 wt. % and preferably from about 0.1 to 10 wt. % of the solution. In any event, these solutions may be diluted with additional water prior to use. In some cases the activity of the active material can be increased by including another agent in the solution, such as glycerin, methylethylcellulose, hydroxyethyl cellulose, polyoxyethylene sorbital mono-oleate, polypropylene glycol, polyacrylic acid, polyethylene sodium malonate, or polyethyleneoxide. The auxiliary occupies generally from about 0.1 to about 5 wt. % and particularly from about 0.5 to 2 wt. % of the solution. The various solutions can in any case also contain an agriculturally suitable surface active agent.

The compounds of the invention can be applied according to any known methods, for example in the form of hydraulic sprays, air sprays or dusts. For methods which involve the application of small volumes, a solution of the compound is generally utilized. The volume used and the rate of application depend upon various factors which vary with the method used, such as the specific type of application method, the stage of development of the plant to which the active ingredient is being applied, and other factors well known to those skilled in the art or easily determined by simple experimentation.

Having now generally described this invention, the same will be better understood by reference to certain specific examples which are included herein for purposes of illustration only and are not intended to be limiting of the invention or any embodiment thereof, unless so specified.

EXAMPLE 1

Synthesis of
1-(4-chlorophenyl)-1,4-dihydro-4-oxo-5-fluorocinnoline-3-carboxylic acid Using the general procedure of Wierenga and Skulnick (J. Org. Chem. 44, 310 (1979)), a solution of 3.0 g (22.6 mmole) of monoethyl malonate in 40 ml of dry THF containing 2 mg of 2,2'-dipyridyl was treated at −75° C. with 29.2 ml of 1.5 M butyllithium (45,28 mmole) in hexane in such a way that the temperature was maintained below −60° C. The temperature was allowed to reach −5° C. and lowered again to −70° at which time 11.32 mmole of 2,6-difluorobenzoyl chloride in 15 ml of dry THF was added while the temperature was maintained at or below −60° C. The mixture was allowed to reach room temperature over 2 hours with continual stirring. After dilution with ether and treatment with 40 ml of 1N HCl the mixture was worked up in the normal fashion to provide after distillation of the organic residue, 6.9 g (67%) of product b.p. 117°–119° C./1 Torr.

A solution of the benzoylacetate (38.8 g, 0.17 mole) in aqueous methanol containing 0.51 mole of potassium acetate, was treated with an aqueous solution of p-chlorophenyldiazonium chloride (derived from 0.18 mole p-chloroaniline) at 10°–15° C. The resulting precipitate was recrystallized from aqueous methanol, dried in vacuo overnight and then dissolved in 300 ml of dry DMF. To this solution was added 11.0 g of anhydrous potassium carbonate and 50 mg of 18-crown-6. The mixture was heated with stirring to 100° for 1 hour. The reaction mixture was cooled and diluted with water, and the precipitate was collected and dried to yield 39 g of the desired cinnoline carboxylate ethyl ester m.p. 158°–160°. The acid desired was obtained by saponification in ethanol at room temperature containing one equivalent of potassium hydroxide, reacidification and filtration of the resulting precipitate, m.p. 246°–247° C.

EXAMPLE 2

Biological Activity

A biological assay for pollen suppression was conducted on the wheat variety W-41 (Anza). This is a heavy tillering wheat which is grown commercially in California. Seeds were planted to provide four plants per 8-inch pot. Plants were raised in a greenhouse until the stage indicated in the following table of results. Three different stages of growth were defined for the purposes of this experiment as follows: Stage 1, spike length of 0.1–0.5 cm; Stage 2, spike length of 0.5–1.5 cm; Stage 3, spike length of 1.5–2.5 cm. External appearance was correlated with the development of the spikelet in order to avoid mistaking the onset of meiosis. Spikelets were removed at various developmental stages and anthers were removed from the most mature florets (which generally occured in about the middle of the spikelet). The anthers were crushed in acetocarmine or propeocarmine and the state of pollen development was assessed. Cytological examinations were made to assess the best time for application. Compounds were applied as solutions in water or water/acetone (5–50% acetone) or as aqueous emulsions. In all cases, 0.1% Triton X-100 was used as a wetting agent. Plants were sprayed to runoff with a test solution and then replaced in such a way that control plants were interspersed with treated plants. Heads were bagged upon emergence and seed set was used as a measure of sterility induction. Compounds that demonstrated good sterilization ability were tested for their effect on female fertility by cross-pollination of awned female plants with awnless male pollen donors.

Control studies were conducted using a known prior art compound (1-(4-chlorophenyl)-1,4-dihydro-4-oxo-6-methylpyridazine-3-carboxylic acid). Optimal dosage and correct stage of application of this compound were determined in order that test crosses could be compared to test crosses made using the compounds of the invention.

Using the general procedure described above, 1-(4-chlorophenyl)-1,4-dihydro-4-oxo-5-fluorocinnoline-3-carboxylic acid potassium salt was screened for pollen suppressing activity.

TABLE 2

| Results of Bioassay | | |
|---|---|---|
| Stage of Application | Dose (ppm) | % Sterility |
| 1 | 125 | 100 |
| 1 | 62.5 | 100 |
| 1 | 31.25 | 100 |
| 1 | 12.5 | 100 |
| 1 | 6.0 | 56 |

Some phytotoxicity was seen by visual examination at dose rates of 31.25 ppm and higher. The effect of representative compounds on female plant fertility is shown in Example 4.

Additionally, 1-(4-chlorophenyl)-1,4-dihydro-4-oxocinnoline-3-carboxylic acid was prepared and tested using the same methods described above. The results of the bioassay for treatment at stage 1 are as follows: dose rate of 250 ppm, 80% male sterility; dose rate of 125 ppm, 26% male sterility.

EXAMPLE 3

Synthesis of Methyl 2,6-difluoro-benzoylacetate

To 3.6 g (25 mmole, 1 eq) of Meldrum's acid and 6.1 g of 4-dimethylamino-pyridine in 60 ml of methylene-chloride was added with stirring, 4.4 g (25 mmole) of 2,6-difluorobenzoylchloride. The temperature was maintained at 0° throughout the addition period and for three additional hours of stirring under argon atmosphere. Most of the methylene chloride was then removed by distillation at 25° or less using a water aspirator to maintain reduced pressure. There was then added 60 ml of anhydrous methanol containing 25 mmole of conc. sulfuric acid.

The mixture was refluxed for three hours, and after concentration in vacuo the residue was taken up in methylene chloride and washed with water. The organic layer was dried over anhydrous $Na_2SO_4$, solvent was removed in vacuo, and the residual oil was distilled to give 4.5 g of desired β-ketoester.

EXAMPLE 4

Preparation of potassium 1-(4'-trifluoromethylphenyl)-5-fluoro-1,4-dihydro-4-oxo-cinnolinecarboxylate To 290 g of 4-aminobenzotrifluoride in 1000 ml of methanol was added 540 ml of conc. hydrochloric acid with ice water cooling. There was then added (at 0°–5°), 124.4 g of $NaNO_2$ in 400 ml of $H_2O$ while stirring was vigorously maintained. The resulting solution of diazonium salt was then added, with stirring at 5°–10°, to a solution of methyl 2,6-difluorobenzoylacetate (321 g) in 2000 ml of methanol containing 441 g of potassium acetate. The resulting precipitate was collected by filtration, dissolved in methylene chloride, and dried over anhydrous sodium sulfate. Solvent was removed in vacuo, and the residual solid was dried further under vacuum overnight at room temperature. The crude adduct (300 g) was then dissolved in 2000 ml of dry dimethylformamide. To this solution was added 118 g of anhydrous $K_2CO_3$ and 100 mg of 18-crown-6. The reaction mixture was then heated with continual stirring to 110°–120° for 1.5 hr under an argon atmosphere. Approximately three-fourths of the solvent was then removed in vacuo at 90° C. The residue was poured into water with stirring. There was obtained 280 g of solid ester after filtration and drying.

Hydrolysis of 280 g of the ester obtained above, in 3000 ml of methanol of containing 64 g of potassium hydroxide, was carried out at room temperature. The resulting potassium salt was obtained by concentration and filtration followed by washing of the solid salt with acetone.

EXAMPLE 4

Field Testing for Pollen Suppression

Compounds were applied in water with suitable surfactants and emulsifiers where necessary. Delivery volumes ranged from 100 to 1000 liters per hectare, and application rates ranged from 0.05 to 10 kg per hectare. Treated plants were surrounded by an untreated pollen donor, and degree of sterilization was monitored by bagging heads of treated plants and counting the number of seeds at maturity. Degree of outcrossing was determined by counting seeds in unbagged heads. A male dominant marker, such as a colored aleurone in the progeny seed, was used to confirm true outcrossing. In some cases the application rate was changed continuously at a known rate along the length of the treated plot.

Results for two compounds of the invention with three varieties of wheat are shown in the following table.

TABLE 3

Field Results for Pollen Suppression With

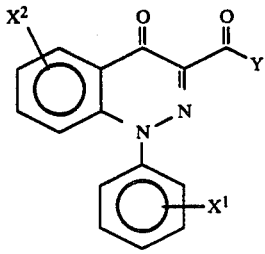

| Variety | Compound | Rate | % Male Sterility | % Female Fertility |
|---|---|---|---|---|
| Marris | $X^1=4'-CF_3$ $X^2=5-F$ | 0.5 kg/ha | 98 | 48.5 |
| Hobbit | $X^1=4'-H$ $X^2=5-F$ | 0.4 kg/ha | 98 | 54 |
| Stephens | $X^1=4'-CF_3$ $X^2=5-F$ | 0.5 kg/ha | 99 | 44 |
|  | $X^1=4'-H$ $X^2=5-F$ | 0.4 kg/ha | 99 | 64 |
| Hill 81 | $X^1=4'-CF_3$ $X^2=5-F$ | 0.5 kg/ha | 99 | 54 |
|  | $X^1=4'-H$ $X^2=5-F$ | 0.4 kg/ha | 98 | 71 |

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A pollen suppressant of the formula wherein
$X^1$ represents hydrogen or one or two substituents independently selected from fluorine, chlorine, bromine, iodine, $C_1$-$C_4$ alkyl, $C_1$-$C_4$ alkoxy, $C_1$-$C_4$ alkanoyl, and trihalomethyl;
$X^2$ represents fluorine or chlorine; and
Y is $OR^3$ wherein $R^3$ is hydrogen, $C_1$-$C_4$ alkyl, $C$-$C_4$ alkenyl, or $C$-$C_4$ alkynyl, and agronomically acceptable salts thereof.

2. The pollen suppressant of claim 1, wherein $X^1$ is hydrogen, 3',4'-dichloro, 4'-methyl, 4'-methoxy, 4'-trifluoromethyl, 4'-iodo, 4'-chloro, 4'-fluoro, 4'-bromo, 3'-fluoro, 3'-chloro, 3'-trifluoromethyl, or 2'-fluoro.

3. The pollen suppressant of claim 1, wherein $X^2$ is fluoro.

4. The pollen suppressant of claim 1, wherein $X^2$ is 5-fluoro or 5-chloro.

5. The pollen suppressant of claim 1, wherein Y is —OH or a salt thereof, —OCH$_3$, or —OCH$_2$CH$_3$.

6. The pollen suppressant of claim 5, wherein $X^2$ is 5-fluoro.

7. The pollen suppressant of claim 6, wherein $X^1$ is hydrogen, 3',4'-dichloro, 4'-methyl, 4'-methoxy, 4'-trifluoromethyl, 4'-iodo, 4'-chloro, 4'-fluoro, 4'-bromo, 3'-fluoro, 3'-chloro, 3'-trifluoromethyl, or 2'-fluoro.

8. The pollen suppressant of claim 1, wherein $X^1$ is 3',4'-diCl, $X^2$ is 5-F, and Y is —OH or a salt thereof.

9. The pollen suppressant of claim 1, wherein $X^1$ is 4'-CH$_3$, $X^2$ is 5-F, and Y is —OCH$_2$CH$_3$.

10. The pollen suppressant of claim 1, wherein $X^1$ is 4'-CH$_3$, $X^2$ is 5-F, and Y is —OH or a salt thereof.

11. The pollen suppressant of claim 1, wherein $X^1$ is 4'-OCH$_3$, $X^2$ is 5-F, and Y is —OH or a salt thereof.

12. The pollen suppressant of claim 1, wherein $X^1$ is 4'-OCH$_3$, $X^2$ is 5-F, and Y is —OCH$_2$CH$_3$.

13. The pollen suppressant of claim 1, wherein $X^1$ is 4'-CF$_3$, $X^2$ is 5-F, and Y is —OCH$_2$CH$_3$.

14. The pollen suppressant of claim 1, wherein $X^1$ is 4'-I, $X^2$ is 5-F, and Y is —OH or a salt thereof.

15. The pollen suppressant of claim 1, wherein $X^1$ is 4'-I, $X^2$ is 5-F, and Y is —OCH$_2$CH$_3$.

16. The pollen suppressant of claim 1, wherein $X^1$ is 4'-Cl, $X^2$ is 5-Cl, and Y is —OH or a salt thereof.

17. The pollen suppressant of claim 1, wherein $X^1$ is 4'-Cl, $X^2$ is 5-Cl, and Y is —OCH$_2$CH$_3$.

18. The pollen suppressant of claim 1, wherein $X^1$ is 4'-F, $X^2$ is 5-F, and Y is —OH or a salt thereof.

19. The pollen suppressant of claim 1, wherein $X^1$ is 3'-F, $X^2$ is 5-F, and Y is —OH or a salt thereof.

20. The pollen suppressant of claim 1, wherein $X^1$ is 3'-F, $X^2$ is 5-F, and Y is —OCH$_2$CH$_3$.

21. The pollen suppressant of claim 1, wherein $X^1$ is 3'-Cl, $X^2$ is 5-F, and Y is —OH or a salt thereof.

22. The pollen suppressant of claim 1, wherein $X^1$ is H, $X^2$ is 5-F, and Y is —OCH$_2$CH$_3$.

23. The pollen suppressant of claim 1, wherein $X^1$ is H, $X^2$ is 5-Cl, and Y is —OH or a salt thereof.

24. The pollen suppressant of claim 1, wherein $X^1$ is 2'-F, $X^2$ is 5-F, and Y is —OH or a salt thereof.

25. The pollen suppressant of claim 1, wherein $X^1$ is 3'-CF$_3$, $X^2$ is 5-F, and Y is —OH or a salt thereof.

26. A method of inducing male sterility in a gramineous plant, which comprises treating said plant, a seed from which said plant is to be grown, or a medium in which said plant is growing or is to be grown with a compound of claim 1.

27. A method of producing hybrid seeds from a self-pollenating gramineous plant which comprises sterilizing the male anthers of a female parent plant with a compound of claim 1 and pollenating said female parent with pollen from an untreated male parent, thereby producing said hybrid seed.

28. The method of claim 27, wherein said hybrid seed is seed from wheat, barley, rye, oats, millet, or corn.

29. The method of claim 28, wherein said seed is wheat seed.

30. The method of inducing male sterility of claim 26, wherein $X^1$ is hydrogen, 3',4'-dichloro, 4'-methyl, 4'-methyoxy, 4'-trifluoromethyl, 4'-iodo, 4'-chloro, 4'-fluoro, 4'-bromo, 3'-fluoro, 3'-chloro, 3'-trifluoromethyl, or 2'-fluoro.

31. The method of inducing male sterility of claim 26, wherein $X^2$ is fluoro.

32. The method of inducing male sterility of claim 26, wherein $X^2$ is 5-fluoro or 5-chloro.

33. The method of inducing male sterility of claim 26, wherein Y is —OH or a salt thereof, —OCH$_3$, or —OCH$_2$CH$_3$.

34. The method of inducing male sterility of claim 33, wherein $X^2$ is 5-fluoro.

35. The method of inducing male sterility of claim 34, wherein $X^1$ is hydrogen, 3',4'-dichloro, 4'-methyl, 4'-methoxy, 4'-trifluoromethyl, 4'-iodo, 4'-chloro, 4'-fluoro, 4'-bromo, 3'-fluoro, 3'-chloro, 3'-trifluoromethyl, or 2'-fluoro.

36. The method of inducing male sterility of claim 27, wherein in $X^1$ is hydrogen, 3',4'-dichloro, 4'-methyl, 4'-methoxy, 4'-trifluoromethyl, 4'-iodo, 4'-chloro, 4'-fluoro, 4'-bromo, 3'-fluoro, 3'-chloro, 3'-trifluoromethyl, or 2'-fluoro.

37. The method of inducing male sterility of claim 27, wherein $X^2$ is fluoro.

38. The method of inducing male sterility of claim 27, wherein $X^2$ is 5-fluoro or 5-chloro.

39. The method of inducing male sterility of claim 27, wherein Y is —OH or a salt thereof, —OCH$_3$, or —OCH$_2$CH$_3$.

40. The method of inducing male sterility of claim 39, wherein $X^2$ is 5-fluoro.

41. The method of inducing male sterility of claim 40, wherein $X^1$ is hydrogen, 3',4'-dichloro, 4'-methyl, 4'-methoxy, 4'-trifluoromethyl, 4'-iodo, 4'-chloro, 4'-fluoro, 4'-bromo, 3'-fluoro, 3'-chloro, 3'-trifluoromethyl, or 2'-fluoro.

* * * * *